United States Patent [19]

Kuss et al.

[11] 3,939,690

[45] Feb. 24, 1976

[54] DEVICE FOR MEASURING FRICTION AND WEAR UNDER SURROUNDING HIGH PRESSURE

[75] Inventors: Eduard Kuss, Hannover; Friedhelm Hotte, Misburg, both of Germany

[73] Assignee: Edward Kuss, Hannover, Germany

[22] Filed: Apr. 16, 1974

[21] Appl. No.: 461,327

[30] Foreign Application Priority Data

Apr. 18, 1973 Germany.......................... 2319668

[52] U.S. Cl. .................................................. 73/9
[51] Int. Cl.² ...................... G01N 3/56; G01N 19/02
[58] Field of Search ................. 73/9, 10, 7, 432 SD

[56] References Cited
UNITED STATES PATENTS

| | | | |
|---|---|---|---|
| 2,177,293 | 10/1939 | Sibley | 73/10 |
| 2,370,606 | 2/1945 | Morgan | 73/10 |
| 2,471,423 | 5/1949 | Gisser | 73/9 |
| 2,539,578 | 1/1951 | Headley | 73/9 |
| 2,867,114 | 1/1959 | Mims | 73/9 |
| 3,302,447 | 2/1967 | Mertwoy | 73/10 |

*Primary Examiner*—Richard E. Aegerter
*Assistant Examiner*—A. J. Mirabito
*Attorney, Agent, or Firm*—John C. Smith, Jr.

[57] ABSTRACT

A device for performing friction and wear tests inside a closed high-pressure autoclave under additional surrounding high pressure adjustable from the outside, wherein a test element arranged inside the autoclave is rotated by means of a driving shaft passed in a pressure-tight manner through the wall of the autoclave into the latter, a contact pressure in the form of an additional unidirectional load is exerted on the test element by means of a unit arranged inside the autoclave, and both the contact pressure and the torsional moment acting on the test element are determined and indicated outside the autoclave.

18 Claims, 9 Drawing Figures

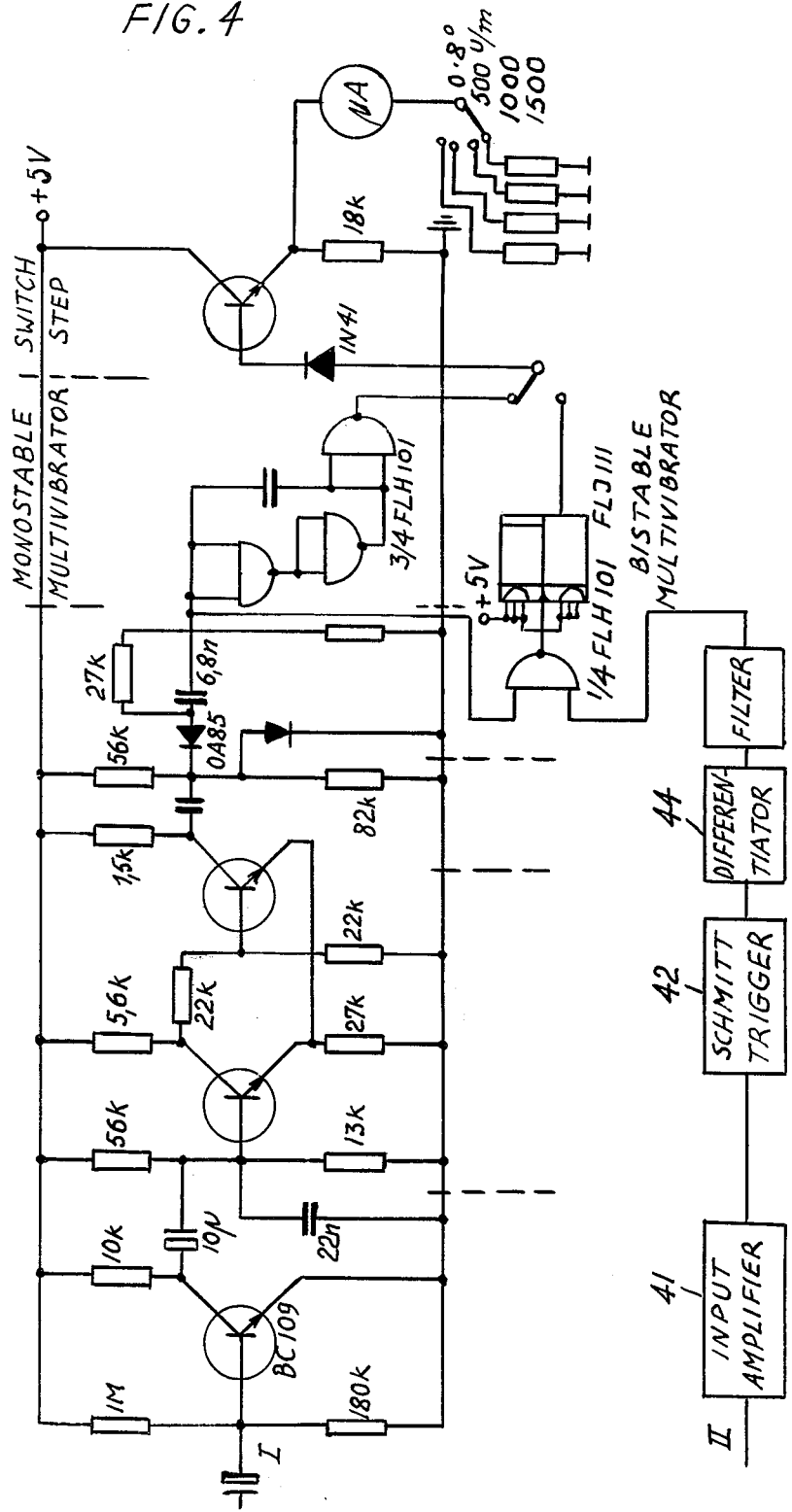

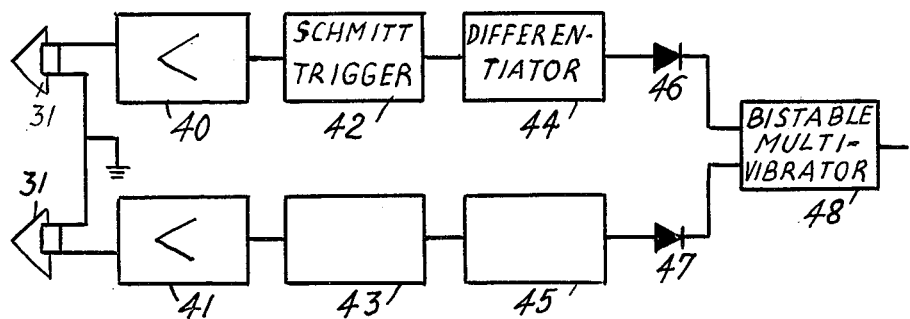
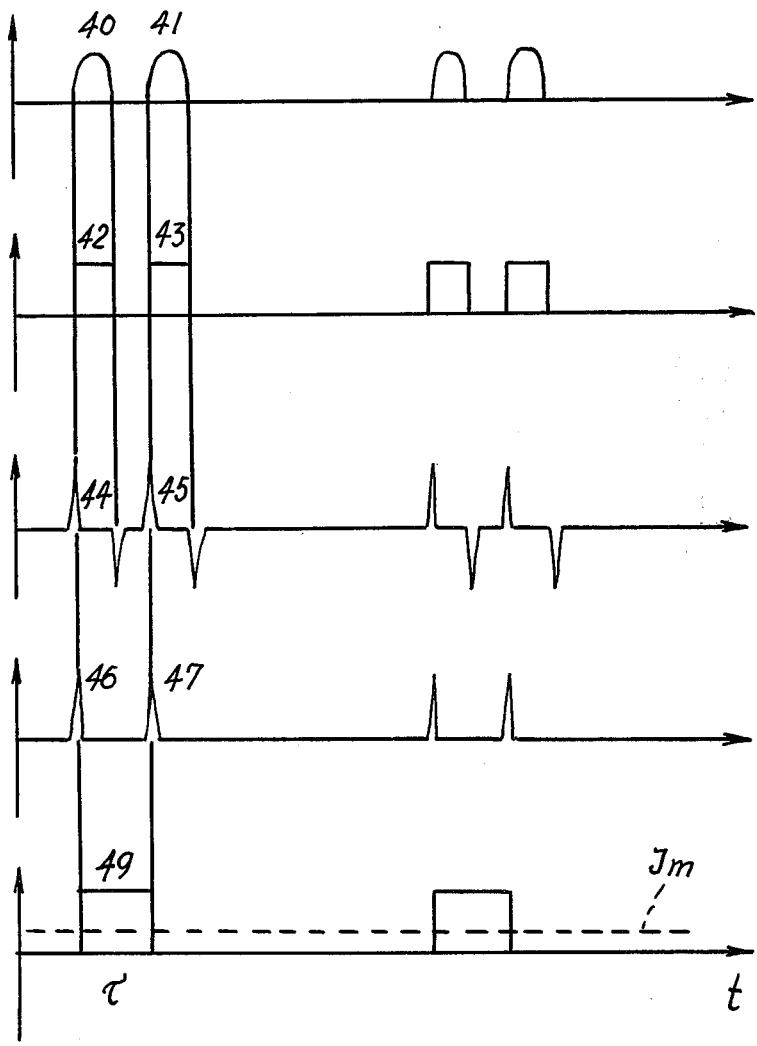

DEVICE FOR MEASURING FRICTION AND WEAR UNDER SURROUNDING HIGH PRESSURE

BACKGROUND OF THE INVENTION

This invention relates to a method of and a device for measuring friction and wear under surrounding high pressure, where balls or rollers are pressed against each other by the measured force of an additional hydraulic unit inside a closed high-pressure autoclave, the torsional moment necessary to maintain the rotary motion is measured inside the autoclave, and in limiting cases the load is determined under which a sudden seizing and welding of the parts occurs.

The extraordinary financial losses yearly produced by friction and wear and the resulting machine damages early led to the development of test machines for determining the oil-quality, the maximum loading capacity of a machine, and the danger of machine damages by laboratory tests. Such test machines are for example: The Four Ball Testing Apparatus, the machines from Timken and Almen-Wieland, The Bartel-Lubrimeter, the Niemann-Gear-Rig (FZG-method), and the new two-disc test stand from Stobel and Niemann.

The often deversified valuation of an oil or lubricant resulting from comparative investigations with different test machines may be an indication that the lubricant should be in the best way adapted to the mechanical design and the specific plant conditions of the machine. Owing to the plurality of the entering parameters (for example geometry of the point of lubrication, surface quality of the machine parts, operating temperature, rotational speed, nominal value of the viscosity, temperature- and pressure-dependence of the viscosity) there is no possibility to constitute a simple scale of quality for lubricants. The lubricant has to be adapted to the considered machine and its characteristic working conditions.

The classical lubrication theory developed by Reynolds, Couette, Sommerfeld, and others already had to discuss the great difficulties, which arise in the theoretical treating of the phenomena of machine lubrication. With several omissions it was possible to develop formulas for the lubricating film-thickness and the coefficient of friction, which for lower machine loads correspond with experimental values and which can be used for the design of the geometrically simple and relative lowly loaded journal bearing.

But the progressive technical evolution led to special gearings showing very high contact pressures. Under these extreme stresses the classical lubrication theory delivers values for lubricating film thickness and coefficient of friction which are about 2 or 3 decimal powers too small. According to this theory mixed friction, wear, seizing, and welding of the machine parts are expected with increasing load, while multifarious experiments still show hydrodynamic lubrication.

As has become known in the meantime the reasons for the failure of the classical theory are the neglecting of the pressure dependence of the lubricant viscosity and the elastic deformation of machine parts under the very high pressure existing at the point of lubrication. These effects are considered by the modern elastohydrodynamic theory of lubrication (EHD-theory). Therewith the great discrepancies between theory and experiment essentially could be eliminated. But in more complicated cases and when the load further increases there are discrepancies and faulty expects in the EHD-theory, too.

It is known for certain that, considering the very complicated pressure- and temperature-shape at the point of lubrication of a machine, the pressure-dependence of the viscosity essentially influences friction and wear. With usual test machines the effects of the separate limiting quantities (pressure- and temperature-dependence of viscosity, compressibility in the whole pressure-temperature-range, geometry of the point of lubrication etc.) cannot be determined in detail. The test result comes about under superposition of several influences.

SUMMARY OF THE INVENTION

It is the object of the present invention to avoid the disadvantages hereinbefore described and to provide a novel method of and device for measuring friction and wear under surrounding high pressure, which method can be performed, as will be described with reference to the following tests, inside a closed autoclave under high external pressure which can be regulated. In consequence of the superposition of the allround hydrostatic pressure it is possible without changing the test system or the lubricant to enhance the basic viscosity by decimal powers and individually to study the influence of basic viscosity, viscosity-pressure-coefficient, temperature, and load on friction and wear over wide ranges.

To perform the tests a high-pressure autoclave is needed, which corresponding to the desired measuring range resists an internal pressure of some thousand bars and which may be as usual constructed as a monoblock tube, shrinkage-tube, wickel-tape-wound cylinder, or multilayer tube. The pressure may be produced by a hand press, a pressure transmitter, or by a continously running compressor.

The propulsion of the test element in the autoclave requires the pressure-tight passing of a rotating shaft through a wall, preferably the removable top wall, of the autoclave. The shaft is sealed by a stuffing-box packing or preferably constructed in the form of a self-sealing shaft as will be described in the following.

GENERATION AND MEASURING OF THE UNILATERAL LOAD

The installed test element, for example a four-ball element adapted to the relative small inside diameter of a high-pressure autoclave or — for studying the conditions under line contact — a unit with a cylindrical or conical shaft and pressed-on counter rollers, has to be able to run under different but always known loads. Therefore there is a hydraulic unit inside the high-pressure autoclave operating under separate pressure. Thus in the test-space being under allround high pressure the rotating balls or rollers of the test element are pressed against each other with a variable power.

The contact pressure and with it the load, under which the test element operates, has to be measured. This principally may happen by a differential-pressure gauge which determines the difference between the pressure inside the hydraulic unit and that inside the autoclave. In this case however the friction at the hydraulic plunger must be taken into account by correction. To avoid this preferably a load cell also being under the allround pressure is mounted between the hydraulic plunger and the balls or rollers being to be pressed. This cell independently from the surrounding pressure determines the unidirectional power out of the elastic deformation of the measuring device via wire strain gauges or selfsupporting resistance transmitters using the usual electronic measuring technique, for example a carrier wave amplifier.

MEASURING OF THE TORSIONAL MOMENT

To determine the friction characteristics the torsional moment transmitted to the test element has to be measured. A measurement on the drive unit arranged outside the autoclave (for example a 5,6 kW-direct-current motor, whose rotational speed may be regulated by thyristor control in the range from 50 to 1500 rpm with accuracy of 0.5 % of final value) is not possible, since the friction of the high-pressure stuffing-box packing would adulterate the measurement.

Therefore the determination of the torsional moment has also to take place inside the high-pressure autoclave independently of the present hydrostatic pressure. For measuring inside the autoclave there is a torsion rod with an appropriate diameter carrying on both ends steel discs with radial grooves. In front of the circumference of the rotating discs scanning heads are mounted, preferable with needle-like permanent magnets and induction coils surrounding the magnets. When a groove is passing, the distance between the magnet and the steel discs changes. The variation of the magnetic current induces a voltage pulse.

In the case of vanishing torsional moment the voltage pulses simultaneously occur on the receivers of both discs. With increasing torsional moment the signals appear corresponding to the distortion of the torsion rod with a phase shifting, which is used for the direct electronic measurement of the torsional moment inside the closed autoclave.

THE PRESSURE-TRANSMITTING INSERT

In order to avoid the necessity of cleaning the whole pressure apparatus with its pressure lines, pressure inducer etc., when the lubricant is exchanged, and in order to do with a relative small quantity of substance of measuring (for example 50 cm$^3$) the test element inside the autoclave is enclosed in a pressure-transmitting insert which transmits the pressure from the surrounding pressure oil to the substance of measurement in the test element and is sealed against the rotating shaft and against the static part and the hydraulic unit producing the contact pressure.

DETERMINATION OF THE WELDING LOAD

At the moment of the welding of the elements, for instance with the four-ball test under pressure, the driving motor is turned off by the thyristor-control unit. In order to avoid damages by still present mass forces a breaker or electromagnetic coupling, which sets the motor free at the moment of welding, may additionally be mounted between the motor shaft and the special stuffing box for the driving shaft.

BRIEF DESCRIPTION OF THE DRAWINGS

A preferred embodiment of the invention will now be described by way of example and with reference to the accompanying drawings, in which:

FIG. 4 is a circuit for torque measurement under pressure;

FIG. 5 is a signal pattern of the torque measurement;

DESCRIPTION OF THE PREFERRED EMBODIMENT

Figure 1:
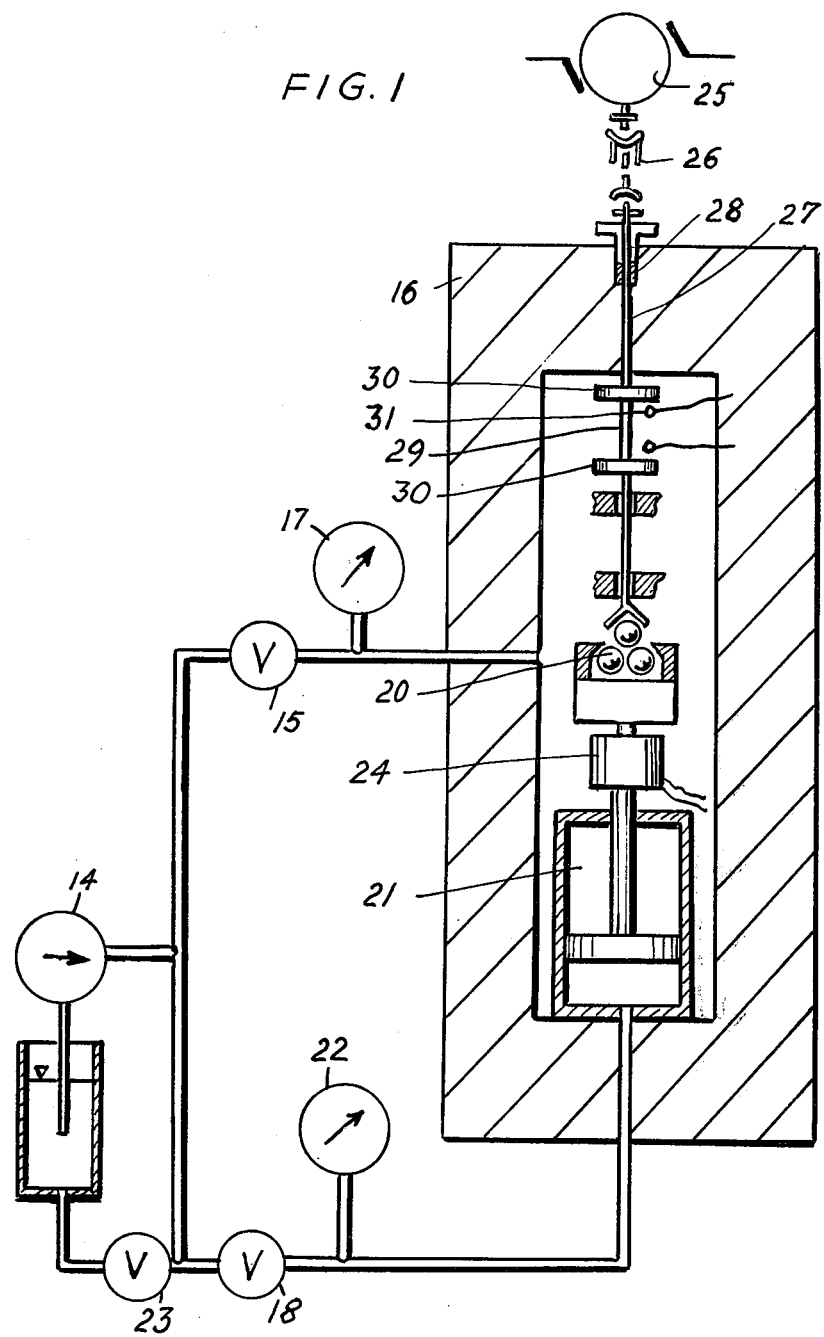
FIG. 1 is a diagrammatic over-all view of an apparatus according to the invention.

FIG. 1 shows a motor-driven compressor 14 arranged to produce depending on its kind of construction pressures of up to 2000 or 5000 bars. With opened valve 15 an autoclave 16 filled with pressure-oil is set under the desired pressure readable on a sensitive pressure gauge 17. Simultaneously a valve 18 is opened so that the interior of a hydraulic unit 21 mounted inside the autoclave 16 is under the same pressure. After closing the valve 15 the pressure in the hydraulic unit 21 can be further raised with the valve 18 being open so that inside the autoclave 16 an additional unidirectional force is created which presses the balls of a four-ball element 20 against each other. Consequently the load during the test-run can be optionally adjusted. The pressure inside the hydraulic unit 21 is readable of a sensitive pressure gauge 22. The pressure difference between the pressure gauges 17 and 22 is an indicator for the load acting on the test element, but the friction at the plunger of the hydraulic unit 21 has to be taken into account.

The suggested construction of the pressure apparatus only needs one high-pressure compressor. The pressure release of the whole apparatus takes place by opening a valve 23.

FIG. 1 also shows the basic construction of the test element inside the autoclave 16. The four-ball element 20 is constructed for measurements under high pressure and is arranged in a pressure-transmitting cell so that different substances can be set in without changing the apparatus. In order to measure exactly the loading of the test machine independently of the surrounding pressure a load cell 24 with free-tensed resistance wires is mounted between the plunger of the hydraulic unit 21 and the plate for the three lower balls of the four-ball element 20.

The upper ball of the four-ball element 20 is driven by a thyristor-controlled motor 25 whose rotational speed is variable over a wide range and the torque of which is transmitted via an overload-shearing clutch 26 and a Cardan shaft to a driving shaft 27 which passes through a special stuffing box 28 provided in the removable top wall of the autoclave 16 in a pressure-tight manner into the latter.

Inside the autoclave 16 there is a device for measuring the torsional moment transmitted to the test element. This device consists of a torsion rod 29, discs 30 attached to this rod and having radial grooves, and two electromagnetic scanning heads 31 connected to leads passing through electrically insulated air-tight passages in the autoclave wall out of the autoclave.

Figure 2:
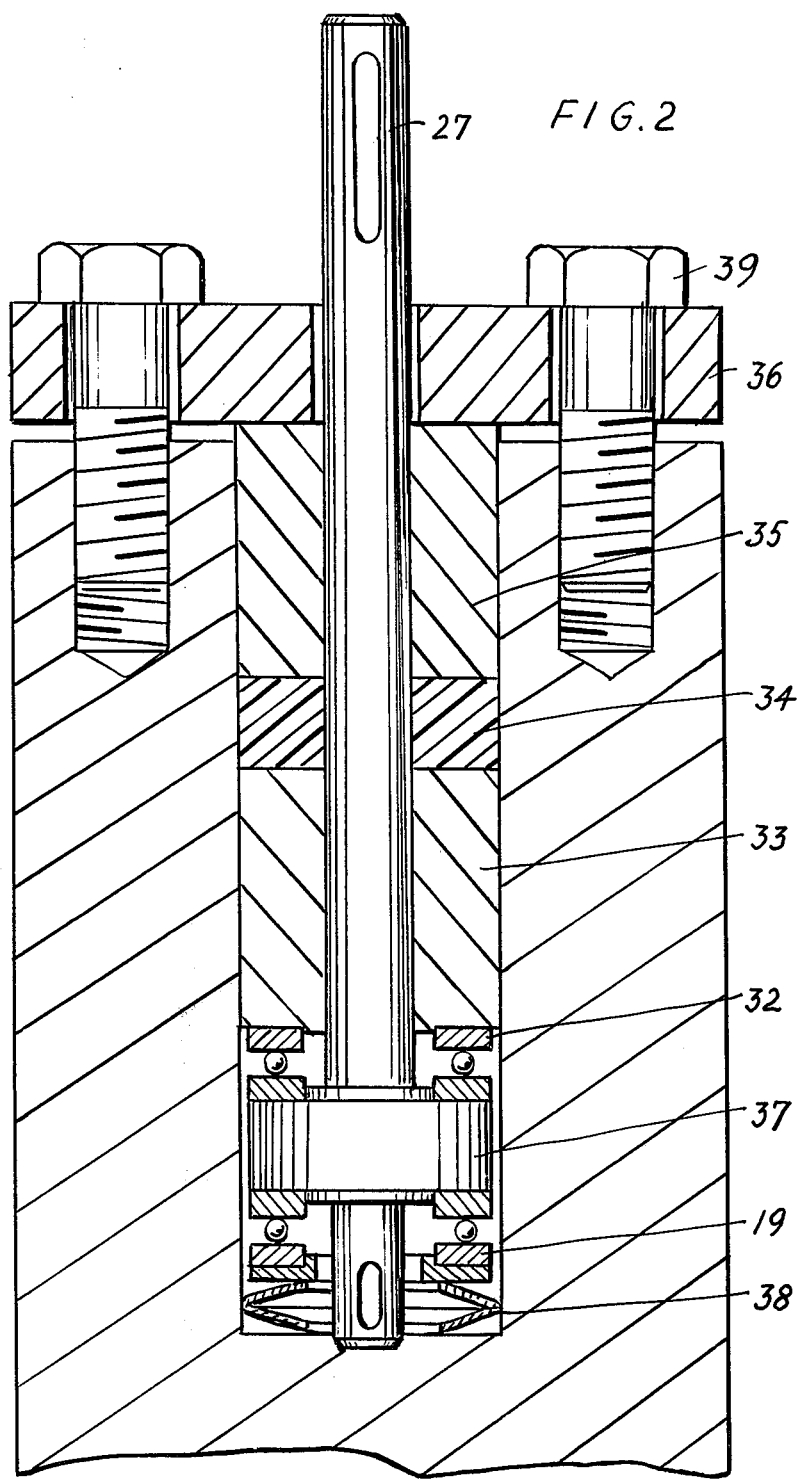
FIG. 2 is a longitudinal section, on a greater scale, of the automatically sealing stuffing box.

FIG. 2 shows the special stuffing box 28 which seals the high-speed driving shaft 27 against the autoclave 16 in the case of pressures of up to 2000 bars.

The sealing is effected in a fully automatic manner because the force of the internal pressure acting on the driving shaft 27 is transmitted via a longitudinal ball bearing 32 to a pressure ring 33. This force and the total force of the internal pressure acting on the ring-shaped area of the pressure ring 33 are transmitted to a sealing ring 34 made of elastic material. Because of the aspect ratio between the total area and the ring-shaped area of the pressure ring 33 the pressure in the sealing ring 34 will be always greater than the internal pressure.

The whole force is then transmitted via a pressure ring 35, a flange 36 and bolts 39 to the casing of the autoclave 16. In order to provide initial pressure for sealing in the lowest pressure range, cup springs 38 are provided which press a collar 37 on the driving shaft 27 via a longitudinal ball bearing 19 against the longitudinal ball bearing 32.

Figure 3:
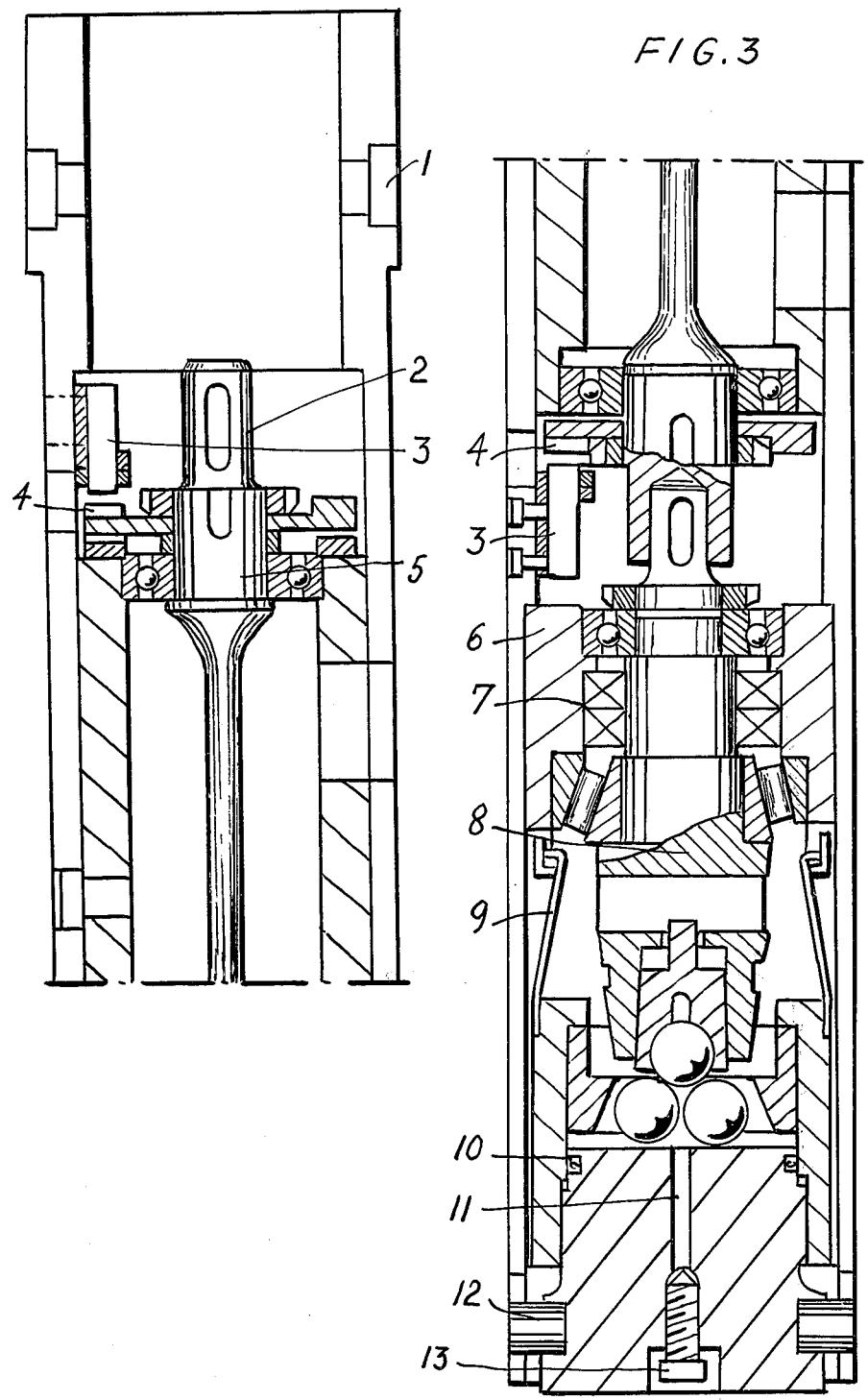
FIG. 3 is a longitudinal section showing the internal structure of the autoclave with the exception of the hydraulic unit and the load cell.

FIG. 3 shows the internal structure of the autoclave 16 with the exception of the hydraulic unit 21 and the load cell 24. A guide tube 1 is fixed to the removable top wall of the autoclave 16 so that the guide tube and the top wall can be mounted at the same time. The reference numeral 2 denotes the shaft end, 3 the scanning heads for the torque-measurement, 4 the grooved steel discs mounted on both ends of the torsion rod 5. The spindle 8 is fulcrumed at the bearing tube 6. The separation of the test substance from the pressure oil takes place dynamically by retaining rings 7 and statically by a hose diaphragm 9 and an O-ring 10. The measuring insert is filled through a bore 11 sealed by a locking screw 13. In the guide tube 1 the ball carrier is suspended by two pins 12 which also receive the counter moment depending on the contact pressure whilst the insert is in operation.

FIG. 4 shows an example of operation for the circuit of the torque-measuring unit. The arrangement determines the phase angle between the signals of the two scanning heads 31 and consequently the transduced torsional moment. Channel I is shown in detail, the identical channel II as a block diagram.

The mode of action of the circuit is shown in FIG. 5. The signals coming from the scanning heads 31 are intensified by input amplifiers 40 and 41. The results are the signals which are shown in the upper diagram of FIG. 5 and which successively appear according to the torsion of the measuring shaft and which are formed to square-wave impulses by the Schmitt-triggers 42 and 43. Behind differentiators 44 and 45 corresponding needle pulses are received, whose negative ones are filtered out by rectifiers 46 and 47. Behind the bistable multivibrator 48 square-wave impulses 49 appear, whose length corresponds to the phase shift $\tau$ between the signals of the scanning heads and whose timely average value Im is shown by a moving-coil instrument with low eigenfrequency. The indication is a direct representation of the torsional moment transmitted to the measuring insert inside the autoclave.

Figure 6A:
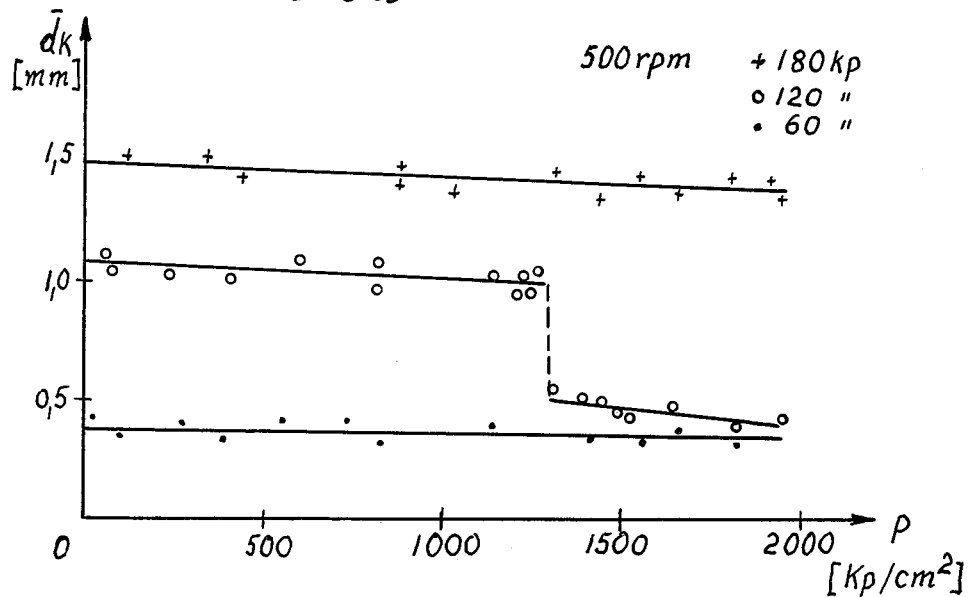
FIGS. 6a and 6b show wear measurements with different loads and rotational speeds under surrounding high pressure
  a. with constant rotational speed of 500 rpm
  b. with constant load of 120 kp.
Figure 6B:
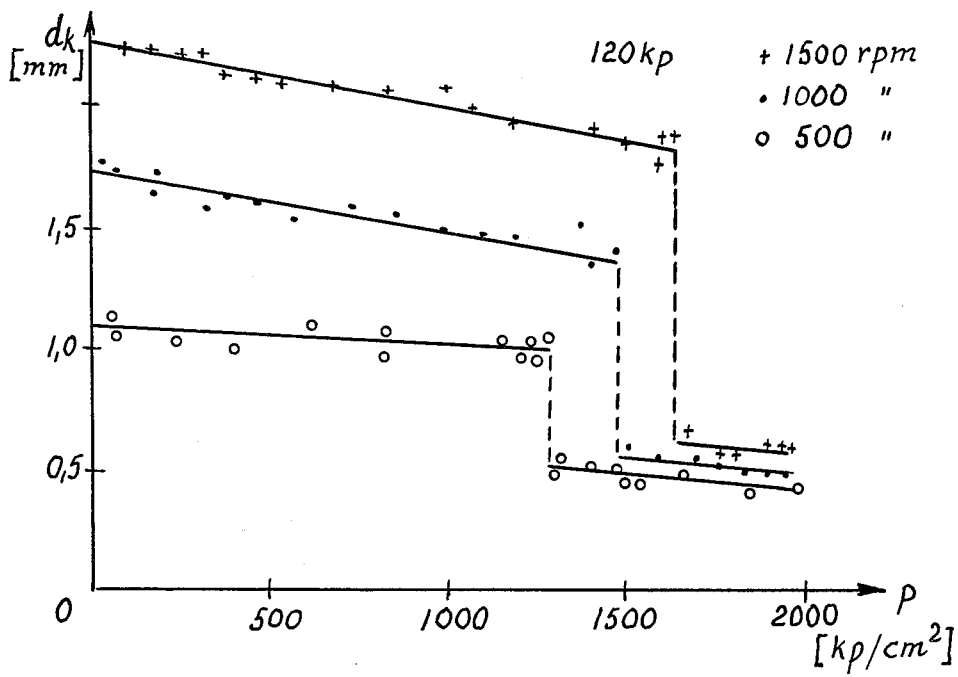

An an example for wear measurements FIGS. 6a and 6b show dependently on pressure p the respective diameter $d_k$ of the wear-cup arising at the test ball. In FIG. 6a measurements are shown performed under constant speed of 500 rpm with different loads of 60, 120 and 180 kp. As shown the machine under the load of 60 kp always is in low position of wear, under the load of 180 kp always in the high position. Under the load of 120 kp there is an abrupt transition from the high to the low position of wear about the pressure of 1300 bars. This directly follows out of the pressure dependence of the viscosity, which is taken into account by the EHD theory with the viscosity-pressure coefficient $\alpha$. According to the lubricant and its viscosity-pressure dependence it is possible to study in detail, how the transition from the high to the low position of wear moves with increasing machine load towards higher pressures.

In the same way it is possible to study the influence of the rotational speed of the machine considered by the lubrication theory. This is shown in FIG. 6b. Under the constant load of 120 kp the transition moves with increasing speed of the machine towards higher pressures. In all cases the loading capacity of the machine raises with increasing pressure. Similarly it is possible to study the wearing loads of the four-ball test dependent on the basic viscosity, the viscosity-pressure coefficient, the temperature-behavior, and the rotational speed.

Figure 7A:
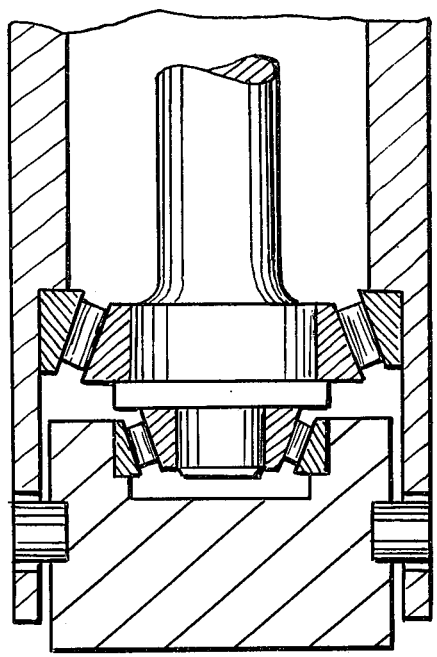
FIGS. 7a and 7b, respectively, show embodiments in which the four-ball element in the pressure-transmitting cell of the autoclave has been replaced by a roller-bearing system and a gear-measuring insert.
Figure 7B:
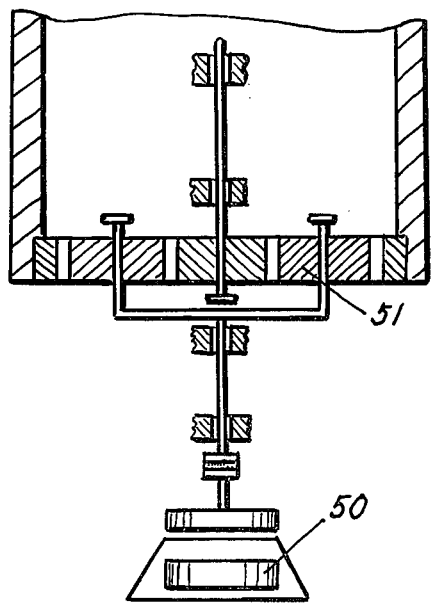

With the same arrangement besides the four-ball system it is further possible to test roller bearings with line contact or gear-mechanisms in a corresponding manner. Therefore only the four-ball element inside the pressure-transmitting cell of the autoclave 16 has to be replaced by a roller- or gear-system. FIG. 7a schematically shows an example for a roller-bearing version, FIG. 7b such one for a feasible gear version 51. In these cases the variable loading is produced by an electrodynamic brake 50 for instance.

With the apparatus according to the invention it is thus possible to perform very different tests including variation of the geometry of the point of lubrication.

The invention may be embodied in other specific forms without departing from the spirit or essential characteristics thereof. The embodiment is therefore to be considered in all respects as illustrative and not restrictive.

What is claimed is:

1. A device for measuring friction and wear under coexisting surrounding high pressure, comprising:
   a. a high-pressure autoclave including walls defining a chamber,
   b. means for supporting at least one test element in said chamber,
   c. a rotatably mounted drive shaft extending through a wall from the exterior to the interior of said chamber and arranged to rotate said support means in said chamber,
   d. a pressure-tight seal between said drive shaft and said wall,
   e. means for applying fluid pressure in said chamber,
   f. means located in said chamber for exerting contact pressure in the form of a unidirectional load on said test element,
   g. means located in said chamber for detecting the torsional moment applied to said test element and comprising a torsional rod extending between said drive shaft and said support means, a pair of magnetized discs spaced on said torsional rod and a pair of stationary inductive scanning heads positioned within said chamber, and
   h. means outside said chamber for indicating both said contact pressure and said torsional moment as detected by said detecting means.

2. A device according to claim 1 wherein said means located in said chamber for exerting contact pressure is a fluid operated means, said means for applying fluid pressure in said chamber being adapted to operate said fluid operated means.

3. A device according to claim 2 wherein said fluid operated means is a piston-cylinder arrangement within said chamber.

4. A device according to claim 1 wherein said means for exerting contact pressure is adapted to apply said pressure in the direction of the rotational axis of said support means.

5. A device according to claim 1 further comprising electrical resistance means located in said chamber for detecting said contact pressure on said test element.

6. A device according to claim 1 further comprising wire strain gauge means located in said chamber for detecting said contact pressure exerted on said test element.

7. A device according to claim 1 further comprising electronic means for converting electrical signals from said scanning heads into square-wave impulses, the length of said impulses corresponding to the phase shift of said signals, and means for indicating said phase shift.

8. A device according to claim 7 wherein said electronic means comprises separate means associated with each scanning head for converting electrical signals from said scanning head into square-wave inpulses and for comparing the length of the square-wave impulses which correspond to the phase shift between the signals of the scanning heads and for indicating the average value thereof.

9. A device according to claim 1 further comprising a driving motor located outside said chamber for driving said drive shaft, said driving motor including electronic means for automatically switching off said driving motor at the moment of welding of test parts.

10. A device according to claim 9 further comprising an overload shearing clutch positioned between said driving motor and said drive shaft, said clutch being adapted to disengage at the moment of welding of test parts.

11. A device according to claim 1 further comprising means for isolating said support means, a portion of said contact pressure means and said test element from the remaining interior portion of said chamber, said isolating means being adapted to transmit said fluid pressure from said chamber into the interior of said isolating means.

12. A device according to claim 1 adapted to test a four-ball test element.

13. A device according to claim 1 adapted to test a roller test element.

14. A device according to claim 1 adapted to test a gear test element.

15. A device for measuring friction and wear under coexisting surrounding high pressure, comprising:
 a. a high-pressure autoclave including walls defining a chamber,
 b. means for supporting at least one test element in said chamber,
 c. a rotatably mounted drive shaft extending through a wall from the exterior to the interior of said chamber and arranged to rotate said support means in said chamber,
 d. a pressure-tight seal between said drive shaft and said wall,
 e. means for applying fluid pressure in said chamber,
 f. means located in said chamber for exerting contact pressure in the form of a unidirectional load on said test element,
 g. means located in said chamber for detecting the torsional moment applied to said test element and comprising a pair of spaced discs rotatably mounted on said drive shaft, each disc including grooves therein, and a pair of stationary scanning heads, and
 h. means outside said chamber for indicating both said contact pressure and said torsional moment as detected by said detecting means.

16. A device according to claim 15 further comprising electronic means for converting electrical signals from said scanning heads into square-wave impulses, the length of said impulses corresponding to the phase shift of said signals, and means for indicating said phase shift.

17. A device according to claim 16 wherein said electronic means comprises separate means associated with each scanning head for converting electrical signals from said scanning head into square-wave impulses and for comparing the length of the square-wave impulses which correspond to the phase shift between the signals of the scanning heads and for indicating the average values thereof.

18. A device for measuring friction and wear under coexisting surrounding high pressure, comprising:
 a. a high-pressure autoclave including walls defining a chamber,
 b. means for supporting at least one test element in said chamber,
 c. a rotatably mounted drive shaft extending through a wall from the exterior to the interior of said chamber and arranged to rotate said support means in said chamber,
 d. a pressure-tight elastic sealing ring between said drive shaft and said wall,
 e. means for applying fluid pressure in said chamber,
 f. means located in said chamber for exerting contact pressure in the form of a unidirectional load on said test element,
 g. means located in said chamber for detecting the torsional moment applied to said test element,
 h. means outside said chamber for indicating both said contact pressure and said torsional moment as detected by said detecting means,
 i. a first pressure ring about said drive shaft at the side of said sealing ring facing away from said chamber,
 j. a second pressure ring about said drive shaft at the side of said sealing ring facing towards said chamber,
 k. a collar mounted on said drive shaft at the side of said second pressure ring facing towards said chamber, and
 l. bearing means between said collar and said second pressure ring,
 m. whereby fluid pressure in said chamber presses said collar against said second pressure ring and presses said second pressure ring against said elastic sealing ring in an axial direction sealing said elastic sealing ring against the peripheral surface of said drive shaft.

\* \* \* \* \*